(12) United States Patent
Marasco

(10) Patent No.: US 12,664,658 B2
(45) Date of Patent: Jun. 23, 2026

(54) HYPERSPECTRAL IMAGING OF BIOFLUIDS FOR BIOMETRIC APPLICATIONS

(71) Applicant: George Mason University, Fairfax, VA (US)

(72) Inventor: Emanuela Marasco, Alexandria, VA (US)

(73) Assignee: George Mason University, Fairfax, VA (US)

( * ) Notice: Subject to any disclaimer, the term of this patent is extended or adjusted under 35 U.S.C. 154(b) by 314 days.

(21) Appl. No.: 18/478,487

(22) Filed: Sep. 29, 2023

(65) Prior Publication Data

US 2024/0177314 A1 May 30, 2024

Related U.S. Application Data

(60) Provisional application No. 63/428,754, filed on Nov. 30, 2022.

(51) Int. Cl.
*G06T 7/00* (2017.01)
*A61B 5/117* (2016.01)
*A61B 5/145* (2006.01)

(52) U.S. Cl.
CPC ............ *G06T 7/0016* (2013.01); *A61B 5/117* (2013.01); *A61B 5/14517* (2013.01); *G06T 2207/10036* (2013.01); *G06T 2207/30088* (2013.01)

(58) Field of Classification Search
CPC ......... G06T 7/0016; G06T 2207/10036; G06T 2207/30088; G06T 7/90; G06T 2207/30196; A61B 5/117; A61B 5/14517; A61B 5/0075
See application file for complete search history.

(56) References Cited

U.S. PATENT DOCUMENTS

2006/0274921 A1* 12/2006 Rowe ................. G06V 40/1324
382/191
2007/0024946 A1* 2/2007 Panasyuk ............... A61B 5/416
359/253
2009/0148005 A1* 6/2009 Rowe ................. G06V 40/1394
382/115

* cited by examiner

*Primary Examiner* — Edward Park
*Assistant Examiner* — Alexander Joseph Vaughn
(74) *Attorney, Agent, or Firm* — Bradley Arant Boult Cummings LLP; Daniel E. Sineway, Esq.

(57) ABSTRACT

Hyperspectral imaging (HSI) of biofluids for biometric applications is disclosed. A HSI device scans a region of a human subject's skin with sweat thereon, without requiring the human subject to touch any surface. The resulting HSI data is processed to identify aspects of the data that represent physical and/or chemical features that uniquely identify the subject. Processing the HSI data includes identifying one or more particular metabolites in the subject's sweat by analyzing wavelengths which those metabolites reflect. Processing the HSI data includes identifying one or more glands beneath the outermost surface of the subject's skin based on HSI-detected wavelength reflectance and wavelength penetration. The disclosed system may generate and store an identity profile corresponding to a human's unique identity features, as determined based on the HSI data processing. A subject's identity is verified by comparing subsequent HSI scans of his skin with sweat thereon to his stored identity profile.

20 Claims, 3 Drawing Sheets

HYPERSPECTRAL IMAGING OF BIOFLUIDS FOR BIOMETRIC APPLICATIONS

CROSS-REFERENCE TO RELATED APPLICATIONS

This application is a Non-Provisional Patent Application of, and claims the benefit of and priority to, Provisional Patent Application No. 63/428,754, filed on Nov. 30, 2022, and entitled "HYPERSPECTRAL IMAGING OF SWEAT FOR BIOMETRIC APPLICATIONS," the disclosure of which is incorporated by reference as if the same were fully set forth herein.

TECHNICAL FIELD

The present systems and processes relate generally to hyperspectral imaging of biofluids for biometric applications, and more specifically to human identity verification by detecting metabolites in sweat via hyperspectral imaging.

BACKGROUND

Current methods for human identity verification typically use either extrinsic features or intrinsic features. Extrinsic features generally include physical biometric information (e.g., facial profiles, eye scans, fingerprints, etc.) or behavioral information (e.g., gait patterns, typing patterns, etc.), which are observable from outside of the body. Intrinsic features generally include physical information measured or detected from within the body, such as heart rate variability, blood vessels underneath the skin, electrocardiogram (ECG) biometrics, electroencephalography (EEG) biometrics, etc. However, it is widely known that using extrinsic and intrinsic features for human identity is an imperfect solution, given their inaccuracies and susceptibilities to spoofing. For example, gait and typing patterns may be imitated, and modern facial recognition systems are known to be inaccurate and discriminatory against minorities (racial and ethnic) and women. Moreover, blood vessels underneath the skin can be imitated by a printouts of finger vein patterns, ECG biometrics can be replicated with previously captured ECG data, and EEG biometrics can be spoofed by imitating a person's mental reaction. While these extrinsic and intrinsic features may successfully verify a human's identity with relative accuracy, they are each nonetheless susceptible to spoofing, which creates risk with respect to cybersecurity, data privacy, and other systems in which security relies on biometric authentication and identity authentication. Therefore, there is a long-felt but unresolved need for systems and processes for human identity verification using biometrics that is both accurate and resilient to spoofing, such as hyperspectral imaging of biofluids for biometric applications.

BRIEF SUMMARY OF THE DISCLOSURE

Briefly described, and according to one embodiment, aspects of the present disclosure generally relate to identity verification based on biometrics and/or biomarkers detected using hyperspectral imaging (HSI). More specifically, embodiments of the present disclosure relate to human identity verification by detecting metabolites or other biochemical compounds in biofluids, namely sweat, via hyperspectral imaging. While sweat as an example biofluid is discussed in great length throughout the present disclosure, such discussion is not intended to limit the claimed embodiments and HSI scanning to only sweat, nor does such discussion preclude other biofluids (such as body serums, or the like) from being scanned for use according to various aspects of the present disclosure.

In various embodiments, the present disclosure discusses novel systems and processes for analyzing chemical properties of a biometric trait. In at least one embodiment, the present disclosure discusses implementing hyperspectral imaging to capture an image of a person's skin, detecting the presence of excreted sweat on the person's skin (as captured in the HSI data), and furthermore processing the HSI-captured image data in order to analyze one or more metabolites in the sweat on the person's skin. In various embodiments, based on the HSI image, the system may be able to not only determine which metabolites are present in the sweat on the person's skin, but also where on the skin the sweat metabolites are present, and respective prevalences and concentrations of the sweat metabolites. Given each person is unique not only in the specific manner in which he/she excretes sweat, but also in the chemical makeup of his/her sweat, analyzing an HSI image of a person's skin and the sweat thereon allows for identifying and extracting unique biometric data that can both accurately verify a person's identity and withstand spoofing efforts.

In various embodiments of the present disclosure, the systems and processes discussed herein employ hyperspectral imaging in a novel, unique, and useful way. Hyperspectral imaging, or HSI, is an imaging technique by which a scanning device (i.e., a camera) captures how a surface reflects individual wavelengths across a spectrum of wavelengths. For example, while a traditional digital camera generally captures and combines the wide wavelength bands of red, green, and blue visible light that are reflected from a surface (the combination of which forms a color visible to the human eye), a hyperspectral imaging device may capture the reflectance (or intensity) of individual wavelengths across a particular range of wavelengths. Accordingly, while a single pixel of an image taken with a digital camera may include the three captured red, green, and blue color values (each typically represented as an integer ranging from 0-255) as detected based on the light reflected from particular point on the surface, a single pixel of an image taken with a HSI device may include the reflectance intensity for each wavelength in the particular range of wavelengths.

In one embodiment, the data captured from HSI scans may be represented as three-dimensional data structures, referred to herein as data cubes or hypercubes, in which the three axes of the data structure may be the x and y axes (corresponding to spatial location on the scanned surface) as well as a wavelength axis (corresponding each wavelength in the scanned range of wavelengths). Given the three-dimensional nature of data cubes generated as a result of HSI scans, the data in the data cube may be analyzed across multiple domains. For example, a single pixel from an HSI scan may be analyzed for reflectance intensity with respect to wavelength, which can be graphically represented as what is referred to as a spectrum graph. In one embodiment, a spectrum graph may include various peaks and valleys corresponding to the reflectance intensity for each wavelength as detected at the location corresponding to a single pixel. In another example, the three-dimensional nature of the data cubes allows for a region of interest (ROI) of the surface captured by the HSI scanner (or the entire surface) to be analyzed based on reflectance intensity for individual wavelengths across the ROI surface as a whole. In this example, a single wavelength's reflectance intensity is mapped across an x vs. y plane (the scanned surface), thus resulting in a picture of the surface that appears to be colored according to the corresponding wavelength (e.g., a blue-like color for the ~450 nm wavelength, a red-like color for the ~720 nm wavelength, etc.), and an image for each wavelength may be analyzed individually (or as a layer of multiple wavelength images).

Moreover, in at least one embodiment, HSI scanners may capture the reflectance of wavelengths outside the visible light spectrum, such as the near-infrared (NIR) spectrum (generally ranging from wavelengths of about 780 nm to 2500 nm). While wavelengths in the visible light spectrum may penetrate human skin to an extent (for example, like what is seen from the top surface of one's finger when shining a bright light upward from the finger's bottom surface), NIR wavelengths may penetrate deeper into the skin than visible light. Accordingly, HSI scanners are capable not only of detecting information on the outermost layer of one's skin, but also of detecting information in subdermal layers (e.g., sweat glands in the dermis, certain tissues in the hypodermis and/or subcutaneous layer, etc.).

In various embodiments, the present systems and processes leverage HSI scanning to match at least a portion of a real-time HSI scan of a human subject's skin to one or more stored templates corresponding to the human subject. In these various embodiments, if certain aspects of the real-time HSI scan are identical, substantially similar, or match within a certain predetermined threshold or degree of confidence, the system may determine that the real-time HSI scan verifies the human's identity (such that the HSI scan confirms that the human is actually who he/she purports to be).

For purposes of example and discussion, consider a scenario in which a HSI scanning system and process as disclosed herein is operatively configured to scan human fingers. In one embodiment, one or more HSI scanning devices included in the system may be contactless scanners, such that a human need not physically touch any surface in order to have his/her finger scanned. Rather, the human may position his/her finger near a HSI scanner such that his/her finger is physically proximate to the HSI scanner but also is suspended in the air. In some embodiments, the HSI scanner may be configured to scan a certain space, and the human may position his/her finger at, on, or near the certain space to allow for the HSI scanner to scan his/her finger.

According to various aspects of the present disclosure, in response to scanning a human's finger, the image data collected from the HSI scanner is transmitted to an electronic computing system for processing. The electronic computing system can be local to the HSI scanner, such that the HSI scanner is directly connected to the electronic computing system via a wired connection or a local wireless network. However, the electronic computing system may also be located remotely from the HSI scanner. For example, in an embodiment in which an HSI scanner is physically located at the entrance to a secure workplace and is configured to scan the fingers of individuals seeking access to the secure workplace, the HSI scanner may transmit the image data (via wireless communication hardware and/or software operatively connected to the HSI scanner) to a remote electronic computing system that may subsequently process the received HSI image data.

As will be discussed further below in association with FIG. 3, the HSI scanner may be configured to scan a human's finger across its entire capable wavelength spectrum, a portion of its capable wavelength spectrum, or at one or more particular wavelengths. For example, if an electronic computing system or an electronic device that is operatively connected to the HSI scanner receives information indicative of a particular human's identity (e.g., a human's identification badge is scanned, detected, or otherwise recognized prior to that human scanning his/her finger with the HSI scanner), the HSI scanner may only scan the human's finger at one or more specific wavelengths based on information already known about the user (e.g., a stored biometric identity profile). In certain embodiments, scanning only one or more specific wavelengths based on known information may provide technical efficiencies given that only relevant data is collected, and thus extraneous data corresponding to other wavelengths need not be collected and processed. In various embodiments, scanning only one or more wavelengths not only reduces the amount of processing resources required (using less data to reach the same conclusion reduces required throughput and frees bandwidth), but also reduces the amount of time required to verify a human's identity based on his/her scanned finger (i.e., lower/faster latency, less given computing is required).

In particular embodiments, the HSI scanner may be configured to scan a human's finger across the entire wavelength spectrum that it is capable of scanning. For example, the present systems and processes disclosed herein may use a Pika-L hyperspectral camera, manufactured by Resonon Inc. in Bozeman, MT, which is capable of scanning for wavelengths across a spectrum ranging from about 400 nm to about 1000 nm. In various embodiments, the HSI scanner may be configured to scan across its full wavelength spectrum during a process in which a biometric identity profile for a human is generated by the system (as discussed in the description further below in association with FIG. 2). For example, in one embodiment, when a human registers with the system, the HSI scanner may capture a full-spectrum image of the human's finger and furthermore process the captured HSI data in order to detect one or more features in the captured HSI data that are uniquely indicative of the human's biochemistry such that future identification of the features (in future HSI scans) could be used to verify the human's identity.

In various embodiments, processing captured HSI data in order to detect one or more features that are unique to a particular human may include analyzing specific wavelengths (or narrow wavelength bands) that are known to indicate the presence of one or more metabolites in human sweat. According to various aspects of the present disclosure, lactate dehydrogenase (LDH), glutamate dehydrogenase (GLDH/GDH), and urea, are metabolites determined to be present in human sweat and therefore may be specifically targeted while processing captured HSI data; however, other metabolites, biomarkers/biometrics, and any relationships between the same, may also be processed for identifying features unique to a human from his/her HSI finger scan data.

In at least one embodiment, LDH, which is an enzyme present in body tissue, has been detected in human sweat samples at a wavelength of 405 nm. Furthermore, in one embodiment, GLDH (an amino acid present in all body tissue) and urea (which is excreted in sweat throughout eccrine glands) have been detected at around 340 nm based on spectrophotometrically-measuring their absorbance per minute.

In some embodiments, the disclosed systems and processes may include applying chemical reagents to a human's finger and capturing an HSI scan of his/her finger subsequent to a HSI scan of his/her finger without the chemical reagent, to confirm (or establish) the specific sweat metabolites present on his/her finger and the concentrations and/or amounts of each metabolite. In various embodiments, the HSI scan of a human's finger with the one or more chemical reagents thereon may be compared to the HSI scan of the human's finger without the chemical reagents thereon to establish correlations between the two sets of HSI data. For example, the HSI scan of a human's finger with the one or more reagents may confirm that a certain pattern present in a wavelength spectrum from the non-reagent HSI data is indicative of a particular sweat metabolite. Put another way, the HSI scan of a human's finger with one or more reagents thereon may establish a baseline, or ground truth, to which features in the non-reagent HSI data can be compared.

In particular embodiments, the disclosed systems and processes may include processing captured HSI data to identify specific glands in a human's finger, and further to map relational distances between each gland. For example, the system may calculate Euclidean distances between multiple points in HSI data, where the multiple points are each indicative of sweat glands located on a human's finger, and such distances (e.g., their distances relative to each other) may be stored as a unique feature (like a biomarker) to verify the user's identity at a future time.

In at least one embodiment, the system may develop and store identity profiles for a plurality of humans based on their HSI finger scans. In various embodiments, the identity profiles may be vectors including one or more uniquely identifiable features, as determined during prior HSI data scan processing. In a particular embodiment, these identity profiles (also referred to throughout the present disclosure as feature vectors and templates) may be compared to subsequently captured HSI finger scans for identity verification purposes.

In one embodiment, the present disclosure discusses a method including: capturing, via a hyperspectral image (HSI) scanner, HSI scan data of a human subject's skin comprising a biofluid thereon, wherein the biofluid was excreted from the human subject's skin; generating a data cube representation of the HSI scan data, wherein the data cube comprises a three-dimensional data structure further comprising a spatial domain and a spectral domain; processing the data cube, wherein processing the data cube comprises detecting one or more signals in the spatial domain and in the spectral domain, wherein the one or more signals are indicative of one or more uniquely identifiable biofluid metabolite features; and generating a feature vector comprising the detected one or more signals indicative of one or more uniquely identifiable biofluid metabolite features, whereby the feature vector is used for subsequent identity verification of the human subject based on the one or more signals indicative of one or more uniquely identifiable biofluid metabolite features.

In addition, the method may include: comparing the feature vector comprising the detected one or more signals indicative of one or more uniquely identifiable biofluid metabolite features to an identity profile to determine a match, wherein the identity profile comprises one or more previously detected signals indicative of one or more uniquely identifiable biofluid metabolite features corresponding to previously captured HSI scan data of a previous human subject's skin comprising the biofluid thereon; and in response to determining a match between the one or more signals indicative of one or more uniquely identifiable biofluid metabolites and the one or more previously detected signals indicative of one or more uniquely identifiable biofluid metabolite features corresponding to previously captured HSI scan data of a previous human subject's skin, determining that the human subject and the previous human subject are the same human subject, thereby verifying the human subject's identity.

In one embodiment, the one or more signals indicative of uniquely identifiable biofluid metabolite features comprise a HSI-detected presence of lactate dehydrogenase, glutamate dehydrogenase, and/or urea in sweat detected above and/or below an outermost skin surface of the human subject's finger. In various embodiments, the lactate dehydrogenase is detected at a wavelength of about 405 nm, and the glutamate dehydrogenase and the urea are detected at a wavelength of about 340 nm.

According to various aspects of the present disclosure, capturing the HSI scan data of the human subject's skin further comprises positioning the human subject's skin in physical proximity to the HSI scanner and within a field of view of the HSI scanner without the human subject's skin making contact with any surface.

In at least one embodiment, the biofluid on the human subject's skin comprises a plurality of metabolites in their natural states and undisturbed by chemical reagents.

In one embodiment, the present disclosure discusses a system comprising: a hyperspectral image (HSI) scanner; and a processor operatively connected to the HSI scanner, wherein the processor is operatively configured to: receive, from the HSI scanner, HSI scan data of a human subject's skin comprising a biofluid thereon, wherein the biofluid was excreted from the human subject's skin; generate a data cube representation of the HSI scan data, wherein the data cube comprises a three-dimensional data structure further comprising a spatial domain and a spectral domain; process the data cube, wherein processing the data cube comprises detecting one or more signals in the spatial domain and in the spectral domain, wherein the one or more signals are indicative of one or more uniquely identifiable biofluid metabolite features; and generate a feature vector comprising the detected one or more signals indicative of one or more uniquely identifiable biofluid metabolite features, whereby the feature vector is used for subsequent identity verification of the human subject based on the one or more signals indicative of one or more uniquely identifiable biofluid metabolite features.

In addition, the processor may be further operable to: compare the feature vector comprising the detected one or more signals indicative of one or more uniquely identifiable biofluid metabolite features to an identity profile to determine a match, wherein the identity profile comprises one or more previously detected signals indicative of one or more uniquely identifiable biofluid metabolite features corresponding to previously captured HSI scan data of a previous human subject's skin comprising the biofluid thereon; and in response to determining a match between the one or more signals indicative of one or more uniquely identifiable biofluid metabolites and the one or more previously detected signals indicative of one or more uniquely identifiable biofluid metabolite features corresponding to previously captured HSI scan data of a previous human subject's skin, determine that the human subject and the previous human subject are the same human subject, thereby verifying the human subject's identity.

In one embodiment, the one or more signals indicative of uniquely identifiable biofluid metabolite features comprise a HSI-detected presence of lactate dehydrogenase, glutamate dehydrogenase, and/or urea in sweat detected above and/or below an outermost skin surface of the human subject's finger. In various embodiments, the lactate dehydrogenase is detected at a wavelength of about 405 nm, and the glutamate dehydrogenase and the urea are detected at a wavelength of about 340 nm.

According to various aspects of the present disclosure, capturing the HSI scan data of the human subject's skin further comprises positioning the human subject's skin in physical proximity to the HSI scanner and within a field of view of the HSI scanner without the human subject's skin making contact with any surface.

In at least one embodiment, the biofluid on the human subject's skin comprises a plurality of metabolites in their natural states and undisturbed by chemical reagents.

In one embodiment, the present disclosure discusses a tangible, non-transitory, computer-readable medium comprising instructions encoded therein, wherein the instructions when executed by a processor, cause the processor to: receive, from a hyperspectral image (HSI) scanner, HSI scan data of a human subject's skin comprising a biofluid thereon, wherein the biofluid was excreted from the human subject's skin; generate a data cube representation of the HSI scan data, wherein the data cube comprises a three-dimensional data structure further comprising a spatial domain and a spectral domain; process the data cube, wherein processing the data cube comprises detecting one or more signals in the spatial domain and in the spectral domain, wherein the one or more signals are indicative of one or more uniquely identifiable biofluid metabolite features; and generate a feature vector comprising the detected one or more signals indicative of one or more uniquely identifiable biofluid metabolite features, whereby the feature vector is used for subsequent identity verification of the human subject based on the one or more signals indicative of one or more uniquely identifiable biofluid metabolite features.

In particular embodiments, the tangible, non-transitory, computer-readable medium may include additional instructions encoded therein, wherein the additional instructions when executed by the processor, further cause the processor to: compare the feature vector comprising the detected one or more signals indicative of one or more uniquely identifiable biofluid metabolite features to an identity profile to determine a match, wherein the identity profile comprises one or more previously detected signals indicative of one or more uniquely identifiable biofluid metabolite features corresponding to previously captured HSI scan data of a previous human subject's skin comprising the biofluid thereon; and in response to determining a match between the one or more signals indicative of one or more uniquely identifiable biofluid metabolites and the one or more previously detected signals indicative of one or more uniquely identifiable biofluid metabolite features corresponding to previously captured HSI scan data of a previous human subject's skin, determine that the human subject and the previous human subject are the same human subject, thereby verifying the human subject's identity.

In one embodiment, the one or more signals indicative of uniquely identifiable biofluid metabolite features comprise a HSI-detected presence of lactate dehydrogenase, glutamate dehydrogenase, and/or urea in sweat detected above and/or below an outermost skin surface of the human subject's finger. In various embodiments, the lactate dehydrogenase is detected at a wavelength of about 405 nm, and the glutamate dehydrogenase and the urea are detected at a wavelength of about 340 nm.

According to various aspects of the present disclosure, capturing the HSI scan data of the human subject's skin further comprises positioning the human subject's skin in physical proximity to the HSI scanner and within a field of view of the HSI scanner without the human subject's skin making contact with any surface.

In at least one embodiment, the biofluid on the human subject's skin comprises a plurality of metabolites in their natural states and undisturbed by chemical reagents.

These and other aspects, features, and benefits of the claimed invention(s) will become apparent from the following detailed written description of the preferred embodiments and aspects taken in conjunction with the following drawings, although variations and modifications thereto may be effected without departing from the spirit and scope of the novel concepts of the disclosure.

BRIEF DESCRIPTION OF THE FIGURES

The accompanying drawings illustrate one or more embodiments and/or aspects of the disclosure and, together with the written description, serve to explain the principles of the disclosure. Wherever possible, the same reference numbers are used throughout the drawings to refer to the same or like elements of an embodiment, and wherein.

DETAILED DESCRIPTION

Figure 1:
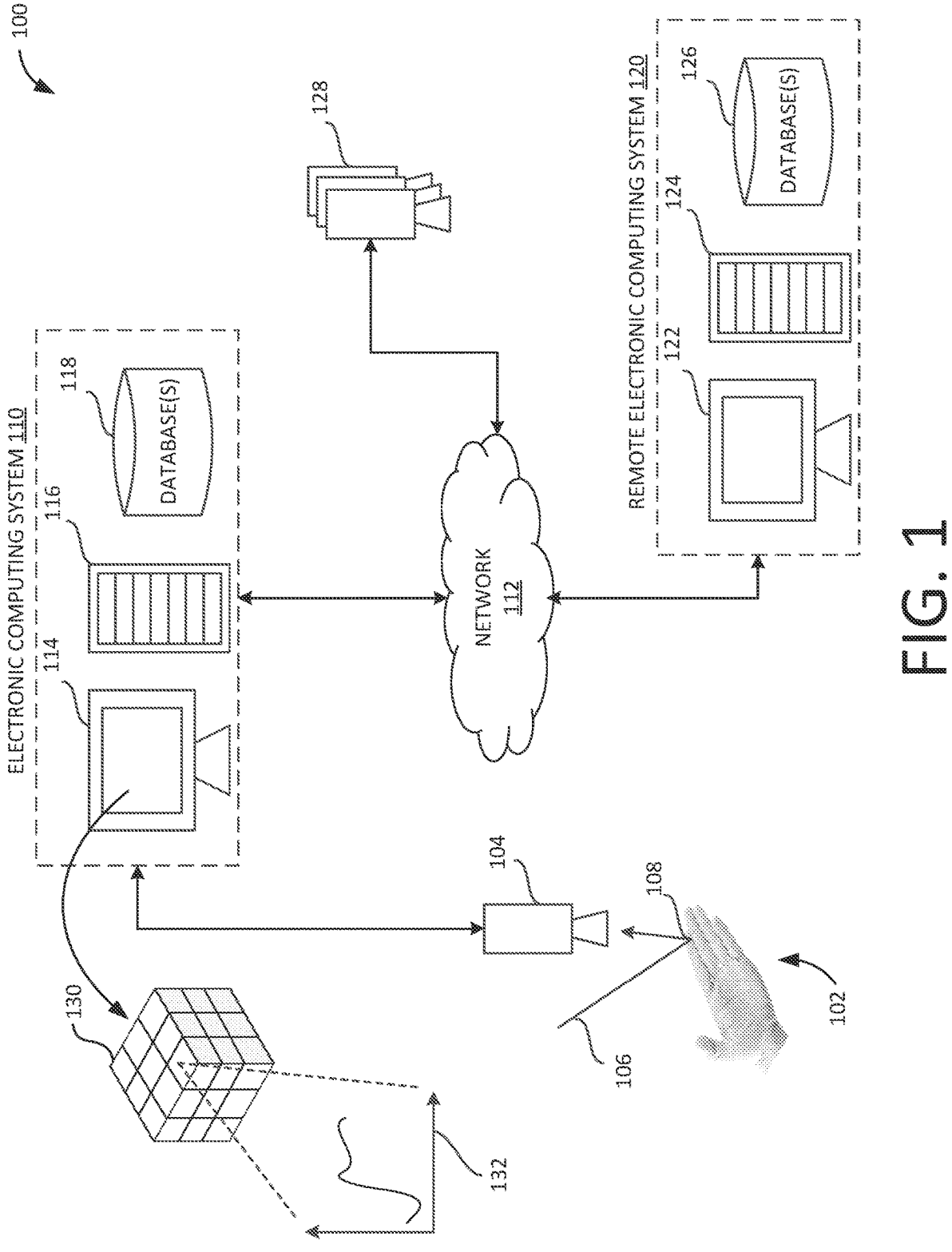
FIG. 1 is a diagram illustrating an example system architecture, according to one aspect of the present disclosure.

For the purpose of promoting an understanding of the principles of the present disclosure, reference will now be made to the embodiments illustrated in the drawings and specific language will be used to describe the same. It will, nevertheless, be understood that no limitation of the scope of the disclosure is thereby intended; any alterations and further modifications of the described or illustrated embodiments, and any further applications of the principles of the disclosure as illustrated therein are contemplated as would normally occur to one skilled in the art to which the disclosure relates. All limitations of scope should be determined in accordance with and as expressed in the claims.

Whether a term is capitalized is not considered definitive or limiting of the meaning of a term. As used in this document, a capitalized term shall have the same meaning as an uncapitalized term, unless the context of the usage specifically indicates that a more restrictive meaning for the capitalized term is intended. However, the capitalization or lack thereof within the remainder of this document is not intended to be necessarily limiting unless the context clearly indicates that such limitation is intended.

Overview

Aspects of the present disclosure generally relate to identity verification based on biometrics and/or biomarkers detected using hyperspectral imaging (HSI). More specifically, embodiments of the present disclosure relate to human identity verification by detecting metabolites or other biochemical compounds in biofluids, namely sweat, via hyperspectral imaging.

In various embodiments, the present disclosure discusses novel systems and processes for analyzing chemical properties of a biometric trait. In at least one embodiment, the present disclosure discusses implementing hyperspectral imaging to capture an image of a person's skin, detecting the presence of excreted sweat on the person's skin (as captured in the HSI data), and furthermore processing the HSI-captured image data in order to analyze one or more metabolites in the sweat on the person's skin. In various embodiments, based on the HSI image, the system may be able to not only determine which metabolites are present in the sweat on the person's skin, but also where on the skin the sweat metabolites are present, and respective prevalences and concentrations of the sweat metabolites. Given each person is unique not only in the specific manner in which he/she excretes sweat, but also in the chemical makeup of his/her sweat, analyzing an HSI image of a person's skin and the sweat thereon allows for identifying and extracting unique biometric data that can both accurately verify a person's identity and withstand spoofing efforts.

In various embodiments of the present disclosure, the systems and processes discussed herein employ hyperspectral imaging in a novel, unique, and useful way. Hyperspectral imaging, or HSI, is an imaging technique by which a scanning device (i.e., a camera) captures how a surface reflects individual wavelengths across a spectrum of wavelengths. For example, while a traditional digital camera generally captures and combines the wide wavelength bands of red, green, and blue visible light that are reflected from a surface (the combination of which forms a color visible to the human eye), a hyperspectral imaging device may capture the reflectance (or intensity) of individual wavelengths across a particular range of wavelengths. Accordingly, while a single pixel of an image taken with a digital camera may include the three captured red, green, and blue color values (each typically represented as an integer ranging from 0-255) as detected based on the light reflected from particular point on the surface, a single pixel of an image taken with a HSI device may include the reflectance intensity for each wavelength in the particular range of wavelengths.

In one embodiment, the data captured from HSI scans may be represented as three-dimensional data structures, referred to herein as data cubes or hypercubes, in which three axes of the data structure may be the x and y axes (corresponding to spatial location on the scanned surface) as well as a wavelength axis (corresponding each wavelength in the scanned range of wavelengths). Given the three-dimensional nature of data cubes generated as a result of HSI scans, the data in the data cube may be analyzed across multiple domains. For example, a single pixel from an HSI scan may be analyzed for reflectance intensity with respect to wavelength, which can be graphically represented as what is referred to as a spectrum graph. In one embodiment, a spectrum graph may include various peaks and valleys corresponding to the reflectance intensity for each wavelength as detected at the location corresponding to a single pixel. In another example, the three-dimensional nature of the data cubes allows for a region of interest (ROI) of the surface captured by the HSI scanner (or the entire surface) to be analyzed based on reflectance intensity for individual wavelengths across the ROI surface as a whole. In this example, a single wavelength's reflectance intensity is mapped across an x vs. y plane (the scanned surface), thus resulting in a picture of the surface that appears to be colored according to the corresponding wavelength (e.g., a blue-like color for the ~450 nm wavelength, a red-like color for the ~720 nm wavelength, etc.), and an image for each wavelength may be analyzed individually (or as a layer of multiple wavelength images).

Moreover, in at least one embodiment, HSI scanners may capture the reflectance of wavelengths outside the visible light spectrum, such as the near-infrared (NIR) spectrum (generally ranging from wavelengths of about 780 nm to 2500 nm). While wavelengths in the visible light spectrum may penetrate human skin to an extent (for example, like what is seen from the top surface of one's finger when shining a bright light upward from the finger's bottom surface), NIR wavelengths may penetrate deeper into the skin than visible light. Accordingly, HSI scanners are capable not only of detecting information on the outermost layer of one's skin, but also of detecting information in subdermal layers (e.g., sweat glands in the dermis, certain tissues in the hypodermis and/or subcutaneous layer, etc.).

In various embodiments, the present systems and processes leverage HSI scanning to match at least a portion of a real-time HSI scan of a human subject's skin to one or more stored templates corresponding to the human subject. In these various embodiments, if certain aspects of the real-time HSI scan are identical, substantially similar, or match within a certain predetermined threshold or degree of confidence, the system may determine that the real-time HSI scan verifies the human's identity (such that the HSI scan confirms that the human is actually who he/she purports to be).

For purposes of example and discussion, consider a scenario in which a HSI scanning system and process as disclosed herein is operatively configured to scan human fingers. In one embodiment, one or more HSI scanning devices included in the system may be contactless scanners, such that a human need not physically touch any surface in order to have his/her finger scanned. Rather, the human may position his/her finger near a HSI scanner such that his/her finger is physically proximate to the HSI scanner but also is suspended in the air. In some embodiments, the HSI scanner may be configured to scan a certain space, and the human may position his/her finger at, on, or near the certain space to allow for the HSI scanner to scan his/her finger.

According to various aspects of the present disclosure, in response to scanning a human's finger, the image data collected from the HSI scanner is transmitted to an electronic computing system for processing. The electronic computing system can be local to the HSI scanner, such that the HSI scanner is directly connected to the electronic computing system via a wired connection or a local wireless network. However, the electronic computing system may also be located remotely from the HSI scanner. For example, in an embodiment in which an HSI scanner is physically located at the entrance to a secure workplace and is configured to scan the fingers of individuals seeking access to the secure workplace, the HSI scanner may transmit the image data (via wireless communication hardware and/or software operatively connected to the HSI scanner) to a remote electronic computing system that may subsequently process the received HSI image data.

As will be discussed further below in association with FIG. 3, the HSI scanner may be configured to scan a human's finger across its entire capable wavelength spectrum, a portion of its capable wavelength spectrum, or at one or more particular wavelengths. For example, if an electronic computing system or an electronic device that is operatively connected to the HSI scanner receives information indicative of a particular human's identity (e.g., a human's identification badge is scanned, detected, or otherwise recognized prior to that human scanning his/her finger with the HSI scanner), the HSI scanner may only scan the human's finger at one or more specific wavelengths based on information already known about the user (e.g., a stored biometric identity profile). In certain embodiments, scanning only one or more specific wavelengths based on known information may provide technical efficiencies given that only relevant data is collected, and thus extraneous data corresponding to other wavelengths need not be collected and processed. In various embodiments, scanning only one or more wavelengths not only reduces the amount of processing resources required (using less data to reach the same conclusion reduces required throughput and frees bandwidth), but also reduces the amount of time required to verify a human's identity based on his/her scanned finger (i.e., lower/faster latency, less given computing is required).

In particular embodiments, the HSI scanner may be configured to scan a human's finger across the entire wavelength spectrum that it is capable of scanning. For example, the present systems and processes disclosed herein may use a Pika-L hyperspectral camera, manufactured by Resonon Inc. in Bozeman, MT, which is capable of scanning for wavelengths across a spectrum ranging from about 400 nm to about 1000 nm. In various embodiments, the HSI scanner may be configured to scan across its full wavelength spectrum during a process in which a biometric identity profile for a human is generated by the system (as discussed in the description further below in association with FIG. 2). For example, in one embodiment, when a human registers with the system, the HSI scanner may capture a full-spectrum image of the human's finger and furthermore process the captured HSI data in order to detect one or more features in the captured HSI data that are uniquely indicative of the human's biochemistry such that future identification of the features (in future HSI scans) could be used to verify the human's identity.

In various embodiments, processing captured HSI data in order to detect one or more features that are unique to a particular human may include analyzing specific wavelengths (or narrow wavelength bands) that are known to indicate the presence of one or more metabolites in human sweat. According to various aspects of the present disclosure, lactate dehydrogenase (LDH), glutamate dehydrogenase (GLDH/GDH), and urea, are metabolites determined to be present in human sweat and therefore may be specifically targeted while processing captured HSI data; however, other metabolites, biomarkers/biometrics, and any relationships between the same, may also be processed for identifying features unique to a human from his/her HSI finger scan data.

In at least one embodiment, LDH, which is an enzyme present in body tissue, has been detected in human sweat samples at a wavelength of 405 nm. Furthermore, in one embodiment, GLDH (an amino acid present in all body tissue) and urea (which is excreted in sweat throughout eccrine glands) have been detected at around 340 nm based on spectrophotometrically-measuring their absorbance per minute.

In some embodiments, the disclosed systems and processes may include applying chemical reagents to a human's finger and capturing an HSI scan of his/her finger subsequent to a HSI scan of his/her finger without the chemical reagent, to confirm (or establish) the specific sweat metabolites present on his/her finger and the concentrations and/or amounts of each metabolite. In various embodiments, the HSI scan of a human's finger with the one or more chemical reagents thereon may be compared to the HSI scan of the human's finger without the chemical reagents thereon to establish correlations between the two sets of HSI data. For example, the HSI scan of a human's finger with the one or more reagents may confirm that a certain pattern present in a wavelength spectrum from the non-reagent HSI data is indicative of a particular sweat metabolite. Put another way, the HSI scan of a human's finger with one or more reagents thereon may establish a baseline, or ground truth, to which features in the non-reagent HSI data can be compared.

In particular embodiments, the disclosed systems and processes may include processing captured HSI data to identify specific glands in a human's finger, and further to map relational distances between each gland. For example, the system may calculate Euclidean distances between multiple points in HSI data, where the multiple points are each indicative of sweat glands located on a human's finger, and such distances (e.g., their distances relative to each other) may be stored as a unique feature (like a biomarker) to verify the user's identity at a future time.

In at least one embodiment, the system may develop and store identity profiles for a plurality of humans based on their HSI finger scans. In various embodiments, the identity profiles may be vectors including one or more uniquely identifiable features, as determined during prior HSI data scan processing. In a particular embodiment, these identity profiles (also referred to throughout the present disclosure as feature vectors and templates) may be compared to subsequently captured HSI finger scans for identity verification purposes.

Example Embodiments

Referring now to the figures, for the purposes of example and explanation of the fundamental processes and components of the disclosed systems and processes, reference is made to FIG. 1, which is a diagram illustrating an exemplary system architecture 100, according to one embodiment of the present disclosure. As will be understood and appreciated, the exemplary system architecture 100 shown in FIG. 1 represents merely one approach or embodiment of the present system, and other aspects are used according to various embodiments of the present system.

As depicted in FIG. 1, the exemplary system architecture 100 (also referred to herein as the system 100), includes various electronic computing components, each of which may be involved in the disclosed novel processes for verifying a human subject's identity based on a HSI scan of his/her skin with sweat thereon. Beginning towards the bottom left corner of FIG. 1, the diagram illustrates a human hand 102 (also referred to herein as the human subject 102, the subject's hand 102, or simply the subject 102) which is positioned under a hyperspectral imaging device 104 (HSI device 104). In at least one embodiment, the HSI 104 device scans the subject's hand 102 with sweat thereon, and the system 100 processes data from the scan to identify one or more uniquely identifying features present in the scan data, such as various metabolites in the sweat on the subject's hand 102. According to various aspects of the present disclosure, the presence of the identified metabolites (and other uniquely identifying biometric features) may be stored within the system 100 as a feature vector (also referred to as an identity profile). In certain embodiments, if the human subject 102 was to receive a subsequent HSI scan, human subject's 102 stored feature vector may be compared to relevant data from the subsequent HSI scan to determine if a match is present between the subsequent scan and the stored feature vector, thereby verifying the human subject's 102 identity.

As mentioned above in the Overview section of the Detailed Description, hyperspectral imaging devices are high-precision imaging devices that are operatively configured to detect the reflectance of one or more wavelengths in the electromagnetic spectrum. Unlike traditional cameras that represent individual pixels of an image as a combination of wide-band red, green, and blue visible light, HSI devices represent each pixel of a scanned image as an individual spectrum of the wavelengths reflected from the point on the subject's hand to which the pixel corresponds. In at least one embodiment, the pixels captured in response to the HSI device 104 scanning the subject's hand 102 may be represented as a three-dimensional data cube in which a spatial dimension (e.g., the x and y axes) is extended into a third spectral dimension (e.g., the wavelength axis). Accordingly, each "layer" of the data cube may correspond to a particular wavelength and the spatial dimension (the x vs. y plane) may represent the reflectance intensity for that particular wavelength as detected by the HSI scanner. In at least one embodiment, the system 100 includes the Pika-L hyperspectral camera which is capable of scanning for wavelengths across a spectrum ranging from about 400 nm to about 1000 nm; however, the system 100 could be configured to use other similarly appropriate devices that are operable to scan for wavelengths across a wider or narrower spectrum.

Continuing with the discussion of FIG. 1, the diagram also illustrates an electromagnetic wave 106 hitting the subject's hand 102, reflecting off the subject's hand 102 at a region of interest 108, and continuing towards the HSI device 104. In various embodiments, the electromagnetic wave 106 may be a combination of wavelengths that are visible to the naked human eye as well as wavelengths that are invisible to the naked human eye (e.g., infrared wavelengths, near-infrared wavelengths, etc.). Moreover, the electromagnetic wave 106 may be supplied by a natural light source (e.g., the sun), or the electromagnetic wave 106 may be specifically produced such that the electromagnetic wave is emanated with a particular intensity and is directed appropriately towards where the HSI device 104 can optimally detect its reflectance.

In at least one embodiment, the region of interest 108 (or ROI 108) may be any area on the human subject's 102 skin which is to be present in the HSI device's 104 field of view during the scanning process. For example, in addition to the human subject's 102 finger, the ROI scanned by the HSI device 104 may include skin on the subject's hand, arm, leg, face, or any other body part that may be positioned near the HSI device 104. According to various aspects of the present disclosure, the ROI 108 is predetermined and may be an area towards the tip of the subject's index fingertip; however, each human subject may have his/her unique ROI to be scanned. In particular embodiments, the ROI 108 may be determined after a scan has been captured, based on certain levels of saturation in the scanned data, or based on other characteristics of the captured scan data.

In response to the electromagnetic wave 106 hitting and reflecting off the subject's hand 102 (and the sweat thereon) at the ROI 108, the HSI device 104 detects the reflectance intensity for each wavelength in the spectrum for which the HSI device is configured to scan. In certain embodiments, the HSI device 104 may be configured to scan only for specific wavelengths, or a subset of its full wavelength spectrum, which will be discussed in greater detail below in association with the discussion of step 302 in the process 300 illustrated in FIG. 3. In particular embodiments, the HSI device 104 is operatively connected to an electronic computing system 110, to which it transmits the data generated from each scan. In one embodiment, the HSI device 104 is operatively connected to the electronic computing system 110 over a wired connection; however, these components (as well as the other components of the system 100) may also be connected over a wireless network 112 (e.g., Wi-Fi, cellular data, broadband, etc.).

In various embodiments, the electronic computing system 110 may be configured to process, store, display, etc., the data received from the HSI device 104. According to various aspects of the present disclosure, the electronic computing system 110 may include computing components such as (but not limited to) a display 114, a processor 116 (or processing unit 116), and a database 118 (or computer memory 118). While, in certain embodiments, the electronic computing system 110 may be physically proximate or local to the HSI device 104, the system 100 may also include remote computing systems 120 which may be configured to handle some, or all, of the computing performed by the electronic computing system 110. The remote electronic computing system 120 may be configured to operate similarly to the electronic computing system 110, and thus the remote electronic computing system may also include computing components such as (but not limited to) a remote display 122, a remote processor 124 (or remote processing unit 124), and a remote database 126 (or remote computer memory 126).

Still continuing with the discussion of FIG. 1, the system 100, in particular embodiments, may include a plurality of field HSI devices 128 that are distributed across various geographical locations. For example, consider a scenario in which a high-security laboratory requires all persons seeking to enter the laboratory to verify his/her identity via the novel systems and process discussed throughout this disclosure. In this example, a field HSI device 128 may be positioned at the laboratory entrance and a verified HSI finger scan may be required prior to entering. The field HSI device 128 may capture the scans, but all processing of the scan (and thus identity verification) may be performed off-site at the remote electronic computing system 120. Accordingly, the field HSI devices 128 may be widely distributed to generally any organization seeking to enhance security procedures and protocols, without also requiring any associated processing requirements.

As mentioned above, scan data transmitted from the HSI device 104 (or a field HSI device 128) to the electronic computing system 110 generally requires subsequent processing to identify uniquely identifiable features in the scan data. In one embodiment, the processor 116 at the electronic computing system 110 is operatively configured to run applications such as Spectronon, which is a software application compatible with the Pika-L HSI device, and which allows for the processor 116 to receive and analyze the scan data transmitted from the HSI device 104. In one embodiment, given the HSI device 104 scans a location over an entire spectrum of wavelengths, the scan data may be represented and processed as a three-dimensional data structure referred to as a data cube 130 (also referred to herein as a hypercube). For ease of understanding, and for purposes of discussion, reference will be made to the data cube 130 as shown in the diagram illustrating the system 100.

In various embodiments, the data cube 130 is illustrated as being a 3×3×3-pixel cube; however, the system may generate data cubes with pixel dimensions in the hundreds, thousands, and higher. For example, the Pika-L may be configured to capture about 900 spatial pixels per scan. According to various aspects of the present disclosure, each square-shaped cell on the top surface of the data cube 130 corresponds to a pixel, and that pixel includes layers of spectrum data captured for each scanned wavelength. Moreover, each layer of spectrum data in a pixel may resemble the spectrum data 132, which illustrates (for discussion purposes and case of understanding) a measure of reflectance intensity (y-axis) across the scanned wavelength spectrum (x-axis). Accordingly, the spectrum data 132 may illustrate, for each pixel across a scanned image or ROI 108, which wavelengths were reflected and a measurement of the reflectance intensity for each wavelength. As will be discussed in greater detail below, certain sweat metabolites reflect specific wavelengths, and therefore not only can these sweat metabolites be identified on the subject's 102 skin, but also data and metadata about the sweat metabolites (e.g., location, concentration, etc.) can be stored as an identity template (or profile) to verify the subject's 102 identity after future HSI scans.

Figure 2:
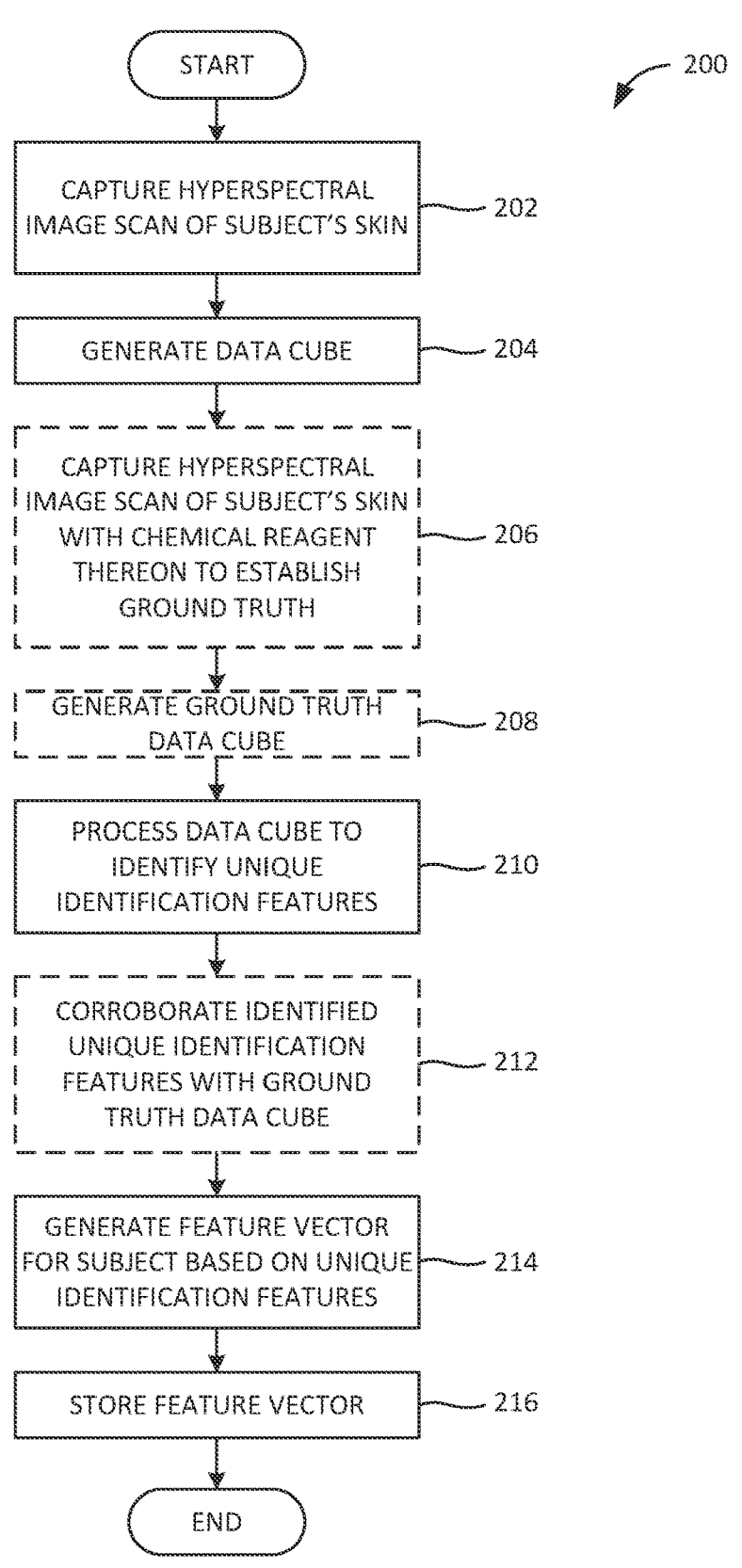
FIG. 2 is a flowchart illustrating an example identity template generation process, according to one aspect of the present disclosure.

Turning now to FIG. 2, a flowchart is shown illustrating an exemplary identity template generation process 200, according to one aspect of the present disclosure. As discussed throughout the present disclosure, embodiments of the novel systems and processes use a HSI device to scan a human subject's skin with sweat thereon to identify sweat metabolites, or other biometric and biomarkers, that may be used for subsequently verifying the human subject's identity. In at least one embodiment, the exemplary identity template generation process 200 discusses the process by which HSI scan data is analyzed for identifying sweat metabolites and other unique identification features, and how the identified sweat metabolites and identification features may subsequently verify a human subject's identity.

In one embodiment, the process 200 begins at step 202, at which the system captures an HSI image scan of a human subject's skin, namely the subject's fingertip. According to various aspects of the present disclosure, step 202 may be the first instance of the subject's finger being scanned, and thus the system, via the HSI device, scans the subject's finger over the HSI device's entire wavelength spectrum in order to generate a complete spectrum profile for the subject. In one embodiment, the system may automatically capture an HSI scan of the subject's finger when it is determined that the subject's finger is an appropriate distance away from the HSI device (e.g., 0.5 inches, 1 inch, 2 inches, 12 inches, etc.). In various embodiments, the system may be configured to capture the HSI scan of the subject's finger in response to determining that a predetermined region of focus, or ROI, is currently within the HSI device's field of view. In at least one embodiment, a ROI may include a rectangular area near the tip of the subject's index finger that encompasses the subject's fingerprint. Accordingly, the system may detect the subject's hand in the HSI's field of view and furthermore recognize (for example, via computer vision tools available through software such as OpenCV or the like) the ROI on the subject's hand, such that the HSI device may focus its scanning on the ROI. In some embodiments, the HSI device itself may be configured to reconfigure its position or orientation (for example, via minor movements with servo motors) to focus the ROI within the HSI device's field of view.

In response to capturing the HSI scan of the subject's finger, the process 200 proceeds to step 204, at which the system generates a data cube representative of the HSI scan. As discussed above in the descriptions of FIGS. 1 and 2, the data captured in response to the HSI device scanning the subject's finger may be represented as a three-dimensional data cube in which a spatial dimension (e.g., the x and y axes) is extended into a third spectral dimension (e.g., the wavelength axis). Accordingly, each "layer" of the data cube may correspond to a particular wavelength and the spatial dimension (the x vs. y plane) may represent the reflectance intensity for that particular wavelength as detected by the HSI scanner. According to various aspects of the present disclosure, generating a data cube allows for the large amount of rich data resulting from the HSI scan to be organized in a data structure that is conducive to processing.

In various embodiments, steps 206 and 208 are both optional steps, such that they are not necessary for the process 200 to execute (or for the system 100 to operate); however, steps 206 and 208 may contribute to higher identity verification success rates (e.g., less false negatives, less false positives, etc.). In one embodiment, step 206 of the process 200 includes the system capturing a HSI image scan of the subject's finger with one or more chemical reagents thereon to obtain ground truth data. In at least one embodiment, mass-spectroscopy-based methods, including bioaffinity systems, have allowed for the measuring of hundreds of metabolites in a single sweat sample by separating metabolites using liquid chromatography and detecting mass-to-charge rations and induced fragmentation for the metabolites. In other embodiments, biocatalytic enzyme cascades may be used to differentiate people based on lactate, urea, and glutamate metabolites detected in sweat, confirming that the levels for each marker sufficiently differs among people. In one embodiment, a ground truth may be established without requiring an HSI scan but instead measuring metabolite levels by applying reagents to swabs, samples, or the like. According to various aspects of the present disclosure, using a chemical reagent to establish a ground truth provides empirical evidence of certain metabolite features in a subject's skin that can be used to confirm the metabolite features detected in non-reagent HSI scans. In certain embodiments, if the system performs step 206, the system may proceed to step 208 at which the system generates a ground truth data cube in the same way as discussed above in step 204.

Proceeding now to step 210, in one embodiment, the system may process the data cube to identify one or more unique identification features. Given the three-dimensional nature of the data cubes, the data structure may be processed and analyzed across multiple domains (spectral and spatial). For example, a single pixel from an HSI scan may be analyzed for reflectance intensity with respect to wavelength (and commonly represented as a spectrum graph). In one embodiment, a spectrum graph may include various peaks and valleys corresponding to the reflectance intensity for each wavelength as measured at the location corresponding to the single pixel. In another example, the three-dimensional nature of the data cubes allows for all pixels that make up a region of interest (ROI) to be concurrently analyzed based on reflectance intensity of each wavelength. In this example, a single wavelength's reflectance intensity is mapped across an x vs. y plane—the ROI—thus resulting in a picture of the ROI that appears to be colored according to the corresponding wavelength and its intensity (e.g., a blue-like color for the ~450 nm wavelength, a red-like color for the ~720 nm wavelength, etc.). Moreover, an image for each wavelength may be analyzed individually (or as a layer of multiple wavelength images).

Continuing with the discussion of step 210, and in light of the above-discussed ways in which the system processes data cubes, the system may process the data cube to detect metabolites in the sweat present on the subject's skin. According to various aspects of the present disclosure, lactate dehydrogenase (LDH), glutamate dehydrogenase (GLD), and urea are metabolites determined to be present in human sweat and therefore their presence may be identified within and extracted from the data cube. In at least one embodiment, LDH, which is an enzyme present in body tissue has been detected in human sweat samples at a wavelength of 405 nm. Furthermore, in one embodiment, GLDH (an amino acid present in all body tissue) and urea (which is excreted in sweat throughout eccrine glands) have been detected at around wavelengths of 340 nm based on spectrophotometrically-measuring their absorbance per minute. Therefore, given these wavelengths are known to reveal unique identifiable data about a subject, both spectral and spatial features associated with these wavelengths may be extracted from the data cube and stored together in a feature vector for subsequent processing.

Still continuing with the discussion of step 210, in at least one embodiment, HSI scanners may capture the reflectance of wavelengths outside the visible light spectrum, such as the near-infrared (NIR) spectrum (generally ranging from wavelengths of about 780 nm to 2500 nm). While wavelengths in the visible light spectrum may penetrate human skin to an extent (for example, what is seen from the top surface of one's finger when shining a bright light from the finger's bottom surface), NIR wavelengths may penetrate deeper into the skin than visible light. Accordingly, HSI scanners are capable not only of detecting information on the outermost layer of one's skin, such as LDH, GLDH, urea, etc., but also of detecting information in subdermal layers such as eccrine sweat glands, and enzymes and amino acids in certain tissues in the hypodermis and/or subcutaneous layer, etc. Therefore, in particular embodiments, the system may detect sweat glands under the skin surface, calculate Euclidean distances between multiple glands or other data points in the HSI data (such as LDH and GLDH presence), and generate a mapping of those distances (e.g., their distances relative to each other) that uniquely identifies the human subject.

In embodiments in which the optional steps 206 and 208 as discussed above were performed, the process 200 may proceed to step 212, at which the system corroborates the identified unique identification features with the ground truth data cube generated at step 208. In various embodiments, using a chemical reagent to establish a ground truth provides empirical evidence of certain metabolite features in a subject's skin, and thus corroborating the identified unique identification features from step 210 with related features in the ground truth data cube can be used to confirm whether one or more metabolite features detected in the non-reagent data cube from step 204 is indeed a unique metabolite feature (and not a false positive feature).

In particular embodiments, the process 200 proceeds to step 214 at which the system generates a feature vector for the subject based on the unique identification features. In various embodiments, the feature vector is a collection of one or more unique identification features that can be used as an identity profile, or template, for verifying the subject's identity based on subsequent HSI scans.

At step 216, the system may store the feature vector. In one embodiment, the system may store the feature vector at the database 118, the remote database 126, in memory closer to the processor for quicker retrieval in anticipation of processing, or within any appropriate computer memory in the system.

Figure 3:
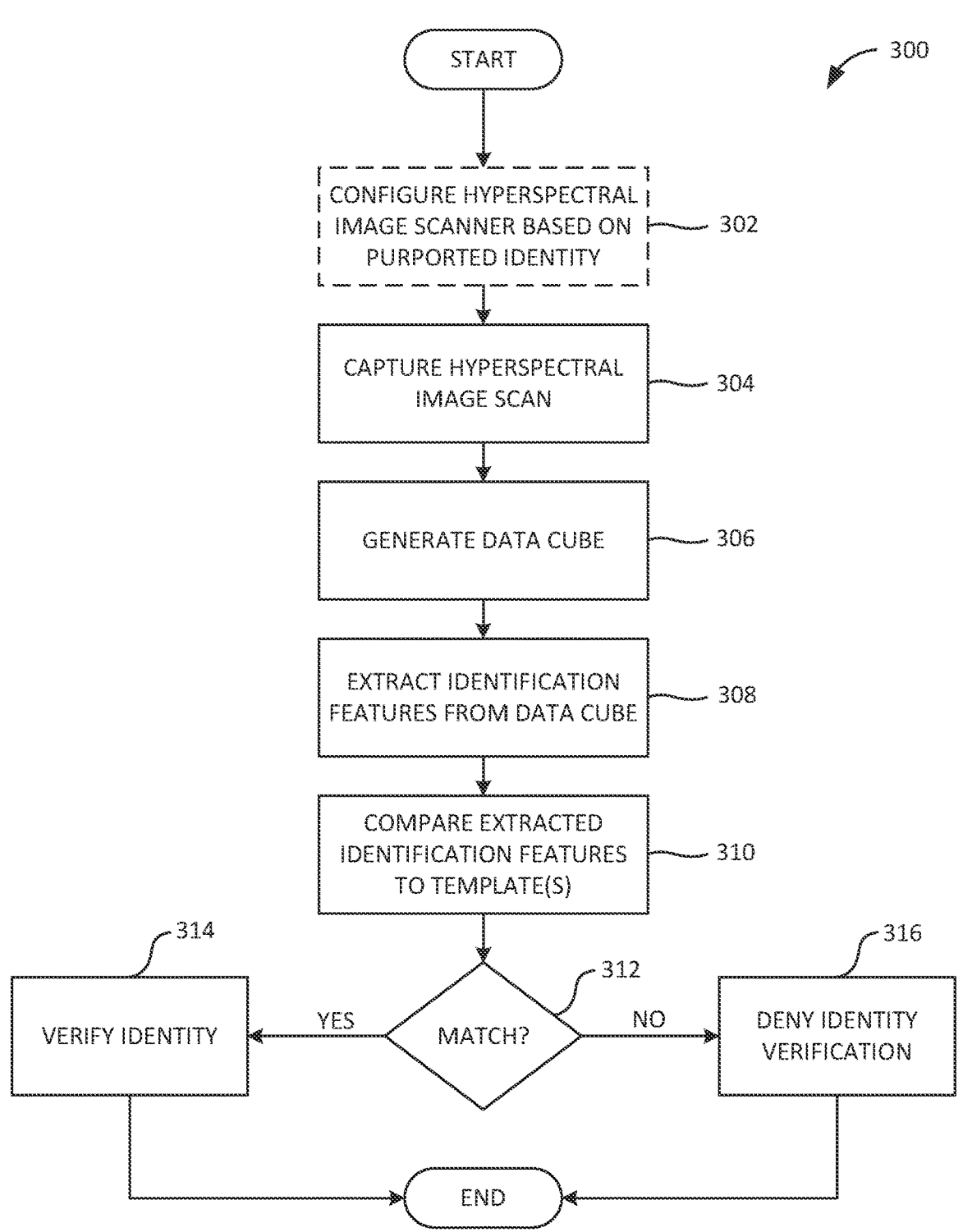
FIG. 3 is a flowchart illustrating an example identity verification process, according to one aspect of the present disclosure.

Turning now to FIG. 3, a flowchart is shown illustrating an exemplary identity verification process 300, according to one aspect of the present disclosure. In general, and in real-life implementations, while the exemplary identity verification process 300 may be performed more frequently than the exemplary identity template generation process 200, the process 300 may only be performed after the process 200 given the process 300 relies on the feature vector (or template) generated at step 214 of the process 200 for verifying a subject's identity. As will be discussed below in connection with the description of the process 200, the process 300 is the process by which a human subject may have his/her identity verified in response to having a HSI scan taken of his/her skin with sweat thereon.

In one embodiment, the process 300 may begin at the optional step 302, at which the system may specifically configure the HSI device prior to scanning a specific subject's skin. As discussed throughout the present disclosure, the HSI devices included in the system (such as HSI device 104 and field HSI device(s) 128) may be operatively configured to perform images scans that measure wavelength reflectance, in a sweeping fashion, from one end of a spectrum to the other end (e.g., from 400 nm to 1000 nm, wavelength-by-wavelength, in a continuous sweep). However, in some embodiments, it may not be practical or required for the system to conduct a full-spectrum scan if the system is provided with data that informs the system of which specific wavelengths to scan, or a subset of wavelengths from the full spectrum to scan, such that the HSI device captures only the required or relevant data for verifying a subject's identity. For example, consider a scenario in which a human subject's finger has already been scanned at least once by the system, such that the system maintains a template identity profile about the human subject, and the template identity profile includes unique identification information about the human subject such as which sweat metabolites were detected on the subject's finger, where on the subject's finger the metabolites were detected, at which wavelengths the sweat metabolites were detected, etc. In this example, if, prior to subsequent scans of the same human subject's finger, the system was system was provided with the human subject's name or purported identity, the system could query the system databases for the human subjects template identity profile (based on the subject's purported identity) and furthermore use the template identity profile to configure the HSI device to scan at only certain wavelengths that are known to produce data matching the template identity profile, and thereby verifying the subject's identity.

Still referring to the optional step 302, and according to various aspects of the present disclosure, the subject's identity profile may also be encoded into an RFID identification badge or the like, such that when the identification badge is scanned for requesting access into a secured area, the subject's identity profile encoded into the identification badge may be transmitted to the system and/or the HSI device physically proximate to the RFID badge scanner. In this embodiment, the system need not query the system databases for the subject's template identity profile. In other embodiments, government-issued identification cards maybe encoded with biometrics or biomarkers such as sweat metabolite features, and thus a subject's government-issued identification cards may be used for configuring HSI scanners immediately prior to scanning the subject's finger.

In various embodiments, the process 300 may continue to (or begin at) step 304. If the optional step 302 was performed, step 304 may be performed according to the specific HSI configuration as determined in step 302. However, in particular embodiments in which the optional step 302 is not performed, the process 300 may begin at step 304 at which the system, via the HSI device, scans the subject's finger over the HSI device's entire wavelength spectrum. In one embodiment, the system may automatically capture an HSI scan of the subject's finger when it is determined that the subject's finger is an appropriate distance away from the HSI device (e.g., 0.5 inches, 1 inch, 2 inches, 12 inches, etc.). In various embodiments, the system may be configured to capture the HSI scan of the subject's finger in response to determining that a predetermined region of focus, or ROI, is currently within the HSI device's field of view. In at least one embodiment, a ROI may include a rectangular area near the tip of the subject's index finger that encompasses the subject's fingerprint, and the rectangular area dimensions may be about as wide and as long as the subject's index finger width. Accordingly, the system may detect the subject's hand in the HSI's field of view and furthermore recognize (for example, via computer vision tools available through software such as OpenCV or the like) the ROI on the subject's hand, such that the HSI device may focus its scanning on the ROI. In some embodiments, the HSI device itself may be configured to reconfigure its position or orientation (for example, via minor movements with servo motors) to focus the ROI within the HSI device's field of view.

In one embodiment, the process 300 proceeds to step 306 at which the system generates a data cube from the HSI scan captured at step 304. As discussed above in the descriptions of FIGS. 1 and 2, the data captured in response to the HSI device scanning the subject's finger may be represented as a three-dimensional data cube in which a spatial dimension (e.g., the x and y axes) is extended into a third spectral dimension (e.g., the wavelength axis). Accordingly, each "layer" of the data cube may correspond to a particular wavelength and the spatial dimension (the x vs. y plane) may represent the reflectance intensity for that particular wavelength as detected by the HSI scanner. According to various aspects of the present disclosure, generating a data cube allows for the large amount of rich data resulting from the HSI scan to be organized in a data structure that is conducive to processing.

At step 308, in various embodiments, the system processes the data cube generated at step 306 to detect and extract identification features from the data cube. Given the three-dimensional nature of the data cubes, the data structure may be processed and analyzed across multiple domains (spectral and spatial). For example, a single pixel from an HSI scan may be analyzed for reflectance intensity with respect to wavelength (and commonly represented as a spectrum graph). In one embodiment, a spectrum graph may include various peaks and valleys corresponding to the reflectance intensity for each wavelength as measured at the location corresponding to the single pixel. In another example, the three-dimensional nature of the data cubes allows for all pixels that make up a region of interest (ROI) to be concurrently analyzed based on reflectance intensity of each wavelength. In this example, a single wavelength's reflectance intensity is mapped across an x vs. y plane—the ROI—thus resulting in a picture of the ROI that appears to be colored according to the corresponding wavelength and its intensity (e.g., a blue-like color for the ~450 nm wavelength, a red-like color for the ~720 nm wavelength, etc.). Moreover, an image for each wavelength may be analyzed individually (or as a layer of multiple wavelength images).

Continuing with the discussion of step 308, and in light of the above-discussed ways in which the system processes data cubes, the system may process the data cube to detect metabolites in the sweat present on the subject's skin. According to various aspects of the present disclosure, lactate dehydrogenase (LDH), glutamate dehydrogenase (GLDH), and urea are metabolites determined to be present in human sweat and therefore their presence may be identified within and extracted from the data cube. In at least one embodiment, LDH, which is an enzyme present in body tissue has been detected in human sweat samples at a wavelength of 405 nm. Furthermore, in one embodiment, GLDH (an amino acid present in all body tissue) and urea (which is excreted in sweat throughout eccrine glands) have been detected at 340 nm based on spectrophotometrically-measuring their absorbance per minute. Therefore, given these wavelengths are known to reveal unique identifiable data about a subject, both spectral and spatial features associated with these wavelengths may be extracted from the data cube and stored together in a feature vector for subsequent processing.

In various embodiments, at step 310 of the process 300, the system compares the identification features extracted from the data cube at step 308 to one or more identity feature templates (as generated at step 214 in the process 200). In particular embodiments, comparing the identification features extracted from the data cube at step 308 to one or more identity feature templates may include determining Pearson correlation coefficients, Euclidean distances between certain features in the data cubes, and angles between spectra. Moreover, algorithms such at the Resonon "Spectra Correlation Matric" function may be used to compute band-to-band correlations. In various embodiments, comparing the identification features extracted from the data cube to the one or more identity feature templates may include machine learning. In at least one embodiment, machine learning models can be trained to identify matches between identification features extracted from data cubes and one or more identity feature templates. For example, in various embodiments, neural networks may be configured, using one or more training data sets, to identify matches between identification features extracted from data cubes and one or more identity feature templates based on statistical probabilities.

In particular embodiments, if some or all of the identification features extracted from the data cube at step 308 are identical to, substantially similar to, or match within a certain predetermined threshold or degree of confidence to the identity feature template belonging to the person the subject purports to be (step 312), the system may determine that the subject's identity is verified (314). However, if differences between the identification features extracted from the data cube at step 308 and the identity feature template belonging to the person the subject purports to be are too great, the system may deny identity verification to the subject (step 316). In various embodiments, the process 300 may conclude after either step 314 or 316; however, in some embodiments, the system may prompt the subject to take a new HSI finger scan and return to step 304 if his/her identity verification was denied at step 316.

From the foregoing, it will be understood that various aspects of the processes described herein are software processes that execute on computer systems that form parts of the system. Accordingly, it will be understood that various embodiments of the system described herein are generally implemented as specially-configured computers including various computer hardware components and, in many cases, significant additional features as compared to conventional or known computers, processes, or the like, as discussed in greater detail herein. Embodiments within the scope of the present disclosure also include computer-readable media for carrying or having computer-executable instructions or data structures stored thereon. Such computer-readable media can be any available media which can be accessed by a computer, or downloadable through communication networks. By way of example, and not limitation, such computer-readable media can comprise various forms of data storage devices or media such as RAM, ROM, flash memory, EEPROM, CD-ROM, DVD, or other optical disk storage, magnetic disk storage, solid state drives (SSDs) or other data storage devices, any type of removable non-volatile memories such as secure digital (SD), flash memory, memory stick, etc., or any other medium which can be used to carry or store computer program code in the form of computer-executable instructions or data structures and which can be accessed by a general purpose computer, special purpose computer, specially-configured computer, mobile device, etc.

When information is transferred or provided over a network or another communications connection (either hardwired, wireless, or a combination of hardwired or wireless) to a computer, the computer properly views the connection as a computer-readable medium. Thus, any such connection is properly termed and considered a computer-readable medium. Combinations of the above should also be included within the scope of computer-readable media. Computer-executable instructions comprise, for example, instructions and data which cause a general purpose computer, special purpose computer, or special purpose processing device such as a mobile device processor to perform one specific function or a group of functions.

Those skilled in the art will understand the features and aspects of a suitable computing environment in which aspects of the disclosure may be implemented. Although not required, some of the embodiments of the claimed systems may be described in the context of computer-executable instructions, such as program modules or engines, as described earlier, being executed by computers in networked environments. Such program modules are often reflected and illustrated by flow charts, sequence diagrams, exemplary screen displays, and other techniques used by those skilled in the art to communicate how to make and use such computer program modules. Generally, program modules include routines, programs, functions, objects, components, data structures, application programming interface (API) calls to other computers whether local or remote, etc. that perform particular tasks or implement particular defined data types, within the computer. Computer-executable instructions, associated data structures and/or schemas, and program modules represent examples of the program code for executing steps of the methods disclosed herein. The particular sequence of such executable instructions or associated data structures represent examples of corresponding acts for implementing the functions described in such steps.

Those skilled in the art will also appreciate that the claimed and/or described systems and methods may be practiced in network computing environments with many types of computer system configurations, including personal computers, smartphones, tablets, hand-held devices, multi-processor systems, microprocessor-based or programmable consumer electronics, networked PCs, minicomputers, mainframe computers, and the like. Embodiments of the claimed system are practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing various aspects of the described operations, which is not illustrated, includes a computing device including a processing unit, a system memory, and a system bus that couples various system components including the system memory to the processing unit. The computer will typically include one or more data storage devices for reading data from and writing data to. The data storage devices provide nonvolatile storage of computer-executable instructions, data structures, program modules, and other data for the computer.

Computer program code that implements the functionality described herein typically comprises one or more program modules that may be stored on a data storage device. This program code, as is known to those skilled in the art, usually includes an operating system, one or more application programs, other program modules, and program data. A user may enter commands and information into the computer through keyboard, touch screen, pointing device, a script containing computer program code written in a scripting language or other input devices (not shown), such as a microphone, etc. These and other input devices are often connected to the processing unit through known electrical, optical, or wireless connections.

The computer that effects many aspects of the described processes will typically operate in a networked environment using logical connections to one or more remote computers or data sources, which are described further below. Remote computers may be another personal computer, a server, a router, a network PC, a peer device or other common network node, and typically include many or all of the elements described above relative to the main computer system in which the systems are embodied. The logical connections between computers include a local area network (LAN), a wide area network (WAN), virtual networks (WAN or LAN), and wireless LANs (WLAN) that are presented here by way of example and not limitation. Such networking environments are commonplace in office-wide or enterprise-wide computer networks, intranets, and the Internet.

When used in a LAN or WLAN networking environment, a computer system implementing aspects of the system is connected to the local network through a network interface or adapter. When used in a WAN or WLAN networking environment, the computer may include a modem, a wireless link, or other mechanisms for establishing communications over the wide area network, such as the Internet. In a networked environment, program modules depicted relative to the computer, or portions thereof, may be stored in a remote data storage device. It will be appreciated that the network connections described or shown are exemplary and other mechanisms of establishing communications over wide area networks or the Internet may be used.

While various aspects have been described in the context of a preferred embodiment, additional aspects, features, and methodologies of the claimed systems will be readily discernible from the description herein, by those of ordinary skill in the art. Many embodiments and adaptations of the disclosure and claimed systems other than those herein described, as well as many variations, modifications, and equivalent arrangements and methodologies, will be apparent from or reasonably suggested by the disclosure and the foregoing description thereof, without departing from the substance or scope of the claims. Furthermore, any sequence(s) and/or temporal order of steps of various processes described and claimed herein are those considered to be the best mode contemplated for carrying out the claimed systems. It should also be understood that, although steps of various processes may be shown and described as being in a preferred sequence or temporal order, the steps of any such processes are not limited to being carried out in any particular sequence or order, absent a specific indication of such to achieve a particular intended result. In most cases, the steps of such processes may be carried out in a variety of different sequences and orders, while still falling within the scope of the claimed systems. In addition, some steps may be carried out simultaneously, contemporaneously, or in synchronization with other steps.

Aspects, features, and benefits of the claimed devices and methods for using the same will become apparent from the information disclosed in the exhibits and the other applications as incorporated by reference. Variations and modifications to the disclosed systems and methods may be effected without departing from the spirit and scope of the novel concepts of the disclosure.

It will, nevertheless, be understood that no limitation of the scope of the disclosure is intended by the information disclosed in the exhibits or the applications incorporated by reference; any alterations and further modifications of the described or illustrated embodiments, and any further applications of the principles of the disclosure as illustrated therein are contemplated as would normally occur to one skilled in the art to which the disclosure relates.

The foregoing description of the exemplary embodiments has been presented only for the purposes of illustration and description and is not intended to be exhaustive or to limit the devices and methods for using the same to the precise forms disclosed. Many modifications and variations are possible in light of the above teaching.

The embodiments were chosen and described in order to explain the principles of the devices and methods for using the same and their practical application so as to enable others skilled in the art to utilize the devices and methods for using the same and various embodiments and with various modifications as are suited to the particular use contemplated. Alternative embodiments will become apparent to those skilled in the art to which the present devices and methods for using the same pertain without departing from their spirit and scope. Accordingly, the scope of the present devices and methods for using the same is defined by the appended claims rather than the foregoing description and the exemplary embodiments described therein.

What is claimed is:

1. A method comprising:
  capturing, via a hyperspectral image (HSI) scanner, HSI scan data of a human subject's skin comprising a biofluid thereon, wherein the biofluid comprises sweat excreted from the human subject's skin;
  generating a data cube representation of the HSI scan data, wherein the data cube comprises a three-dimensional data structure further comprising a spatial domain and a spectral domain;
  processing the data cube, wherein processing the data cube comprises;
    detecting one or more signals in the spatial domain and in the spectral domain, wherein the one or more signals are indicative of one or more uniquely identifiable biofluid metabolite features, and wherein the one or more uniquely identifiable biofluid metabolite features comprise at least one of lactate dehydrogenase, glutamate dehydrogenase, and urea present in the biofluid;
    detecting one or more points in the spatial domain, wherein the one or more points are indicative of one or more glands in a subdermal layer of the human subject's skin; and
    calculating at least one Euclidean distance between the one or more points; and
  generating a feature vector comprising the detected one or more signals indicative of one or more uniquely identifiable biofluid metabolite features and the at least one Euclidean distance between the one or more points, whereby the feature vector is used for subsequent identity verification of the human subject based on the one or more signals indicative of one or more uniquely identifiable biofluid metabolite features.

2. The method of claim 1, further comprising:
comparing the feature vector comprising the detected one or more signals indicative of one or more uniquely identifiable biofluid metabolite features and the at least one Euclidean distance to an identity profile to determine a match, wherein the identity profile comprises one or more previously detected signals indicative of one or more uniquely identifiable biofluid metabolite features and at least one previously calculated Euclidean distance corresponding to previously captured HSI scan data of a previous human subject's skin comprising the biofluid thereon; and
in response to determining a first match between the one or more signals indicative of one or more uniquely identifiable biofluid metabolites and the one or more previously detected signals indicative of one or more uniquely identifiable biofluid metabolite features and a second match between the at least one Euclidean distance and the at least one previously calculated Euclidean distance corresponding to previously captured HSI scan data of a previous human subject's skin, determining that the human subject and the previous human subject are the same human subject, thereby verifying the human subject's identity.

3. The method of claim 1, wherein the one or more signals indicative of uniquely identifiable biofluid metabolite features comprise a HSI-detected presence of the lactate dehydrogenase, the glutamate dehydrogenase, and/or the urea in the sweat detected above and/or below an outermost skin surface of the human subject's finger.

4. The method of claim 3, wherein the lactate dehydrogenase is detected at a wavelength of about 405 nm.

5. The method of claim 3, wherein the glutamate dehydrogenase and the urea are detected at a wavelength of about 340 nm.

6. The method of claim 1, wherein capturing the HSI scan data of the human subject's skin further comprises positioning the human subject's skin in physical proximity to the HSI scanner and within a field of view of the HSI scanner without the human subject's skin making contact with any surface.

7. The method of claim 1, wherein the biofluid on the human subject's skin comprises a plurality of metabolites in their natural states and undisturbed by chemical reagents.

8. A system comprising:
  a hyperspectral image (HSI) scanner; and
  a processor operatively connected to the HSI scanner, wherein the processor is operatively configured to:
    receive, from the HSI scanner, HSI scan data of a human subject's skin comprising a biofluid thereon, wherein the biofluid comprises sweat excreted from the human subject's skin;
    generate a data cube representation of the HSI scan data, wherein the data cube comprises a three-dimensional data structure further comprising a spatial domain and a spectral domain;
    process the data cube, wherein processing the data cube comprises:
      detecting one or more signals in the spatial domain and in the spectral domain, wherein the one or more signals are indicative of one or more uniquely identifiable biofluid metabolite features and the one or more uniquely identifiable biofluid metabolite features comprise at least one of lactate dehydrogenase, glutamate dehydrogenase, and urea present in the biofluid;

detecting one or more points in the spatial domain, wherein the one or more points are indicative of one or more glands in a subdermal layer of the human subject's skin; and calculating at least one Euclidean distance between the one or more points; and generate a feature vector comprising the detected one or more signals indicative of one or more uniquely identifiable biofluid metabolite features, whereby the feature vector is used for subsequent identity verification of the human subject based on the one or more signals indicative of one or more uniquely identifiable biofluid metabolite features.

9. The system of claim 8, wherein the processor is further operatively configured to:

compare the feature vector comprising the detected one or more signals indicative of one or more uniquely identifiable biofluid metabolite features and the at least one Euclidean distance to an identity profile to determine a match, wherein the identity profile comprises one or more previously detected signals indicative of one or more uniquely identifiable biofluid metabolite features and at least one previously calculated Euclidean distance corresponding to previously captured HSI scan data of a previous human subject's skin comprising the biofluid thereon; and in response to determining a first match between the one or more signals indicative of one or more uniquely identifiable biofluid metabolites and the one or more previously detected signals indicative of one or more uniquely identifiable biofluid metabolite features and a second match between the at least one Euclidean distance and the at least one previously calculated Euclidean distance corresponding to previously captured HSI scan data of a previous human subject's skin, determine that the human subject and the previous human subject are the same human subject, thereby verifying the human subject's identity.

10. The system of claim 8, wherein the one or more signals indicative of uniquely identifiable biofluid metabolite features comprise a HSI-detected presence of the lactate dehydrogenase, the glutamate dehydrogenase, and/or the urea in the sweat detected above and/or below an outermost skin surface of the human subject's finger.

11. The system of claim 10, wherein the lactate dehydrogenase is detected at a wavelength of about 405 nm.

12. The system of claim 10, wherein the glutamate dehydrogenase and the urea are detected at a wavelength of about 340 nm.

13. The system of claim 8, wherein capturing the HSI scan data of the human subject's skin further comprises positioning the human subject's skin in physical proximity to the HSI scanner and within a field of view of the HSI scanner without the human subject's skin making contact with any surface.

14. The system of claim 8, wherein the biofluid on the human subject's skin comprises a plurality of metabolites in their natural states and undisturbed by chemical reagents.

15. A tangible, non-transitory, computer-readable medium comprising instructions encoded therein, wherein the instructions when executed by a processor, cause the processor to:

receive, from a hyperspectral image (HSI) scanner, HSI scan data of a human subject's skin comprising a biofluid thereon, wherein the biofluid comprises sweat excreted from the human subject's skin;

generate a data cube representation of the HSI scan data, wherein the data cube comprises a three-dimensional data structure further comprising a spatial domain and a spectral domain;

process the data cube, wherein processing the data cube comprises:

detecting one or more signals in the spatial domain and in the spectral domain, wherein the one or more signals are indicative of one or more uniquely identifiable biofluid metabolite features and the one or more uniquely identifiable biofluid metabolite features comprise at least one of lactate dehydrogenase, glutamate dehydrogenase, and urea present in the biofluid;

detecting one or more points in the spatial domain, wherein the one or more points are indicative of one or more glands in a subdermal layer of the human subject's skin; and calculating at least one Euclidean distance between the one or more points; and generate a feature vector comprising the detected one or more signals indicative of one or more uniquely identifiable biofluid metabolite features and at the at least one Euclidean distance between the one or more points, whereby the feature vector is used for subsequent identity verification of the human subject based on the one or more signals indicative of one or more uniquely identifiable biofluid metabolite features.

16. The tangible, non-transitory, computer-readable medium of claim 15 comprising additional instructions encoded therein, wherein the additional instructions when executed by the processor, further cause the processor to:

compare the feature vector comprising the detected one or more signals indicative of one or more uniquely identifiable biofluid metabolite features and the at least one Euclidean distance to an identity profile to determine a match, wherein the identity profile comprises one or more previously detected signals indicative of one or more uniquely identifiable biofluid metabolite features and at least one previously calculated Euclidean distance corresponding to previously captured HSI scan data of a previous human subject's skin comprising the biofluid thereon; and in response to determining a first match between the one or more signals indicative of one or more uniquely identifiable biofluid metabolites and the one or more previously detected signals indicative of one or more uniquely identifiable biofluid metabolite features and a second match between the at least one Euclidean distance and the at least one previously calculated Euclidean distance corresponding to previously captured HSI scan data of a previous human subject's skin, determine that the human subject and the previous human subject are the same human subject, thereby verifying the human subject's identity.

17. The tangible, non-transitory, computer-readable medium of claim 15, wherein the one or more signals indicative of uniquely identifiable biofluid metabolite features comprise a HSI-detected presence of the lactate dehydrogenase, the glutamate dehydrogenase, and/or the urea in the sweat detected above and/or below an outermost skin surface of the human subject's finger.

18. The tangible, non-transitory, computer-readable medium of claim 17, wherein the lactate dehydrogenase is detected at a wavelength of about 405 nm, and wherein the glutamate dehydrogenase and the urea are detected at a wavelength of about 340 nm.

19. The tangible, non-transitory, computer-readable medium of claim 15, wherein capturing the HSI scan data of the human subject's skin further comprises positioning the human subject's skin in physical proximity to the HSI scanner and within a field of view of the HSI scanner without the human subject's skin making contact with any surface.

20. The tangible, non-transitory, computer-readable medium of claim 15, wherein the biofluid on the human subject's finger comprises a plurality of metabolites in their natural states and undisturbed by chemical reagents.

\* \* \* \* \*